(12) United States Patent
Lesea-Ames

(10) Patent No.: US 8,529,409 B1
(45) Date of Patent: Sep. 10, 2013

(54) MOBILE PERSONAL FITNESS TRAINING

(76) Inventor: Jennifer Lesea-Ames, Lafayette, CO (US)

( * ) Notice: Subject to any disclaimer, the term of this patent is extended or adjusted under 35 U.S.C. 154(b) by 1135 days.

(21) Appl. No.: 11/464,104

(22) Filed: Aug. 11, 2006

Related U.S. Application Data

(60) Provisional application No. 60/775,684, filed on Feb. 22, 2006.

(51) Int. Cl.
*A63B 71/00* (2006.01)

(52) U.S. Cl.
USPC .................................... 482/9; 482/8

(58) Field of Classification Search
USPC ............... 482/1, 3–9, 901, 902; 434/247
See application file for complete search history.

(56) References Cited

U.S. PATENT DOCUMENTS

| | | | |
|---|---|---|---|
| 5,213,555 A * | 5/1993 | Hood et al. | 482/57 |
| 6,605,038 B1 * | 8/2003 | Teller et al. | 600/300 |
| 7,013,175 B2 * | 3/2006 | Dardik et al. | 600/520 |
| 7,041,032 B1 * | 5/2006 | Calvano | 482/4 |
| 7,056,265 B1 * | 6/2006 | Shea | 482/8 |
| 7,254,516 B2 * | 8/2007 | Case et al. | 702/182 |
| 2005/0107216 A1 * | 5/2005 | Lee et al. | 482/8 |
| 2005/0197063 A1 * | 9/2005 | White | 455/41.2 |
| 2005/0202934 A1 * | 9/2005 | Olrik et al. | 482/8 |
| 2005/0209050 A1 * | 9/2005 | Bartels | 482/8 |
| 2006/0205564 A1 * | 9/2006 | Peterson | 482/8 |
| 2007/0219059 A1 * | 9/2007 | Schwartz et al. | 482/8 |
| 2008/0051256 A1 * | 2/2008 | Ashby et al. | 482/5 |
| 2008/0096726 A1 * | 4/2008 | Riley et al. | 482/8 |

* cited by examiner

*Primary Examiner* — Oren Ginsberg
(74) *Attorney, Agent, or Firm* — Duft Bornsen & Fettig, LLP

(57) ABSTRACT

Systems and methods presented herein generally provide for portable personalized training programs. More specifically, a mobile device (e.g., MP3 players, iPods, video game players, PDAs, cell phones, etc.) may provide to a user of the device a personalized physical fitness training program that enables the user to maintain physical fitness. In this regard, a physical fitness training program may be configured as one or more software modules wherein associated audio and video segments allow a user to view various physical fitness related training routines on the mobile device. The physical fitness training program may operably control these audio and video segments in a manner that allows the user to personalize a physical fitness routine. Such systems and methods may also have advantages and other types of personalized instruction.

1 Claim, 7 Drawing Sheets

MOBILE PERSONAL FITNESS TRAINING

CROSS REFERENCE TO RELATED APPLICATIONS

This patent application claims priority to and thus the benefit of an earlier filing date from U.S. Provisional Patent Application No. 60/775,684 (filed Feb. 22, 2006 and entitled "Systems and Methods for Maintaining Physical Fitness"), the entire contents of which are hereby incorporated within by reference.

TECHNOLOGICAL FIELD

Systems and methods presented herein generally relate to providing personalized instruction, such as personalized fitness training, via a mobile device (e.g., a cell phone, a portable media player, Personal Digital Assistant—PDA, etc.). More specifically, the mobile device may be configured with a physical fitness software program that retrieves and/or configures personalized physical fitness training routines for a user of the device. The software program may also be web-based or configured with a network terminal, for example, in a health club setting.

BACKGROUND

Physical fitness has become a tremendously large industry particularly due to an increased attention to health. As such, many systems and methods have been developed to enable a user to stay physically fit so that a user could exercise within the confines of home. For example, a myriad of workout videos, with choreographed fitness routines, were produced at the advent of the VCR and then the DVD player. These types of workouts offer personal training to the masses albeit without any particular customization. Accordingly, there has been a noticeably growing trend in the use of certified personal fitness trainers that tailor physical fitness programs for their clients.

Society in general has become exceptionally busy. Even though the desire to stay healthy through physical fitness is there, people often have trouble allocating time to do so. In this regard, people are now using certified personal fitness trainers more often. For example, the use of certified personal fitness trainers, a practice formerly reserved for celebrities and the wealthy, has become more prevalent among other social classes with greater time constraints. That is, members of these other social classes generally have less time due to work and family obligations. Because certified personal fitness trainers are often able to help people focus on physical fitness routines, the time spent on those routines can be dramatically reduced. As such, certified personal fitness trainers can help people stay healthy in less time.

Still, the use of certified personal fitness trainers may require time that is not available to many people, as most personal training sessions are 60-minutes in duration For example, people often travel to places such as gyms to have access to personal trainers. To circumvent this problem, certified personal fitness trainers may visit people to assist them with their physical fitness needs. However, this "personal fitness on demand" approach is often very expensive, as certified personal fitness trainers charge for their travel time to the client's home.

SUMMARY

Systems and methods presented herein generally provide for portable physical fitness training programs for maintaining and/or improving a user's physical fitness level. In one embodiment, a mobile device provides for portable physical fitness training programs for the user of the device. Examples of such devices include cell phones, PDAs, laptop computers, portable media players (e.g., MP3 players, such as iPods by Apple Inc., and video game players), etc. In this regard, a physical fitness training program may be configured as one or more software modules wherein associated audio and video segments allow a user to view various physical fitness related training programs on a mobile device.

Additionally, the software modules may configure the audio and video segments in a manner that essentially customizes a physical fitness routine for a user. For example, the mobile device may be configured with a user interface that allows the user to input data to the software modules. The software modules may use this data to create a user profile and subsequently configure a specific physical fitness program for the user. Alternatively or additionally, the user profile may be used to retrieve a particular physical fitness program from storage that corresponds to parameters within the user profile. In addition, a user can have the option of selecting video clips of exercises of their choice to download these video clips into the portable viewing device. For example, the video clips may illustrate a particular strength training exercise, a yoga pose, or a rehabilitation exercise prescribed by a licensed physical therapist (e.g., a therapist that is licensed through the state in which they are practicing). Generally, the software modules of the physical fitness program direct a processor to present audio and video data (e.g., JPEG, MPEG, etc.) at various times within the training regimen. In this regard, the physical fitness program may be configured with several different types of computing devices (e.g., cell phones, PDAs, portable media players, laptop computers, desktop computers, etc.). However, the physical fitness program is preferably configured with mobile devices (e.g., cell phones, PDAs, portable media players, video game devices, etc.) to improve the mobility of personalized fitness training.

The types of audio and video data may include "clips" of such data provided by actual certified personal fitness trainers (e.g., personal fitness trainers that are certified by American College of Sports Medicine, National Strength and Conditioning Association, and American Council on Exercise are national certifications or even uncertified personal trainers). For example, each physical fitness program may include previously recorded routines being performed by professional fitness trainers. These clips may be parsed by a fitness program operating module to enable a user to customize a physical fitness routine. In other words, previously recorded clips of various exercises performed by professional trainers may be processed along with user entered parameters by the fitness program operating module to deliver a personalized physical fitness routine. In this regard, the physical fitness routine provides the advantages of a certified personal trainer without the need for and/or expense of visiting the fitness professional.

Additionally, the physical fitness program may include additional output features that enable the user to download the personalized routine to recordable formats. For example, the physical fitness program may include a software module that allows for a personalized physical fitness routine to be displayed with a display element of the device operating the routine. The software module may also allow for the personalized physical fitness routine to be stored on a processor readable media for observation at a later time. An example of such may include a Digital Video Disc (DVD) wherein the personalized physical fitness routine may be displayed on a television or a computer. In this regard, the physical fitness program may be configured to operate on a general purpose computer such that a certified personal fitness trainer may configure a personalized physical fitness routine for a user and burn that to a DVD for the user to view at a later time. Alternatively, the user may also operate the physical fitness program to burn the personalized physical fitness routine to a DVD for subsequent viewing. Other examples of processor readable media include compact discs (CDs), computer hard drives, and portable RAM devices.

Another feature of the present invention includes a system for selecting, for example, an exercise machine at a health club, and downloading a video file that contains instructions and/or a demonstration on how to use the exercise machine from a data server. This system has the advantage of allowing a user to learn the correct technique for performing an exercise without the need for and/or expense of a certified personal fitness trainer. This feature can be implemented in a variety of ways.

For example, a user may select a particular exercise machine by using the mobile device to scan a barcode placed on the machine at a particular health club. Then the barcode data identifying the machine may be sent by the mobile device via a communication interface to a data server operated by the health club. In this regard, the data server may maintain video files and associated instructions on the operation of the exercise machine. The data server may then receive and interpret the barcode data and transmit an instructional program corresponding to the particular exercise machine to the mobile device via the communication interface so that the video may be viewed by the user. The communication interface between the mobile device and the data server may be any suitable interface, examples of such may include USB, WiFi, Bluetooth, Cellular, et cetera.

Those skilled in the art will recognize that there are various other methods for selecting an exercise machine. For example, each machine could be identified by a name or number that the user could select using an input interface the mobile device. In another example, the user could take a photo of the machine using a camera attached to or embedded in the mobile device, and the data server may be configured to recognize the selected exercise machine from the photo or text recognition on the machine, and send the corresponding video to the mobile device.

The embodiment described above is merely one system for implementing the present feature. The video file sent by the data server may be accompanied by an audio file, depending on a number of factors (e.g., user preference, storage space availability, type of mobile device, et cetera). Additionally, the user may select more than one exercise machine at a time. For example, a user may select any or all of the exercise machines at a particular health club to be downloaded to a mobile device from the data server. Furthermore, this feature is not limited to instructional videos pertaining to the use of exercise machines. Other examples of instructional videos that may be selected by a user include stretching exercises, yoga poses, rehabilitation exercises, et cetera.

In one embodiment, a mobile device provides one or more software programs to a user, wherein the mobile device includes a processor, a storage element, a data interface, an audio output, and a display element, wherein the mobile device provides one or more software programs to a user via an operating system, and wherein at least one of the software programs is a fitness program. The fitness program includes a user profile module that receives information about a user via the data interface, the display element, or both, wherein the user profile module configures a user profile based on the received information and wherein the user profile is stored with the storage element and includes at least one physiological parameter and a fitness instruction module that processes at least one fitness instruction parameter and provides fitness instruction to the user via the audio output and the display element based on the user profile and the at least one fitness instruction parameter. The physiological parameter may be age, sex, height, weight, body fat percentage, resting heart rate, blood pressure, and/or body temperature.

The mobile device may be a cell phone, personal digital assistant, digital media player, a mobile gaming device, a laptop computer, or a tablet computer. The data interface may be an RF interface; infrared interface; Ethernet interface; Universal serial bus interface; Bluetooth interface; FireWire interface; and an Ipod dock connector.

The display element includes a touch screen interface, wherein the user profile module receives user entries entered through the touch screen interface and transfers the user entries to the fitness instruction module, wherein the fitness instruction module processes the user entries to configure one or more operational parameters for the fitness instruction. The one or more operational parameters may, for example, include duration, type of exercise, intensity, and/or frequency. The fitness program may further include a data acquisition module that communicatively couples to the data interface and the display element to receive the user profile.

The user profile module may include a data acquisition module communicatively coupled to the data interface, the display, or both to receive the information about a user. The fitness program may include an output module that records the fitness instruction on a processor readable media. The processor readable media may be a DVD, a compact disc, a computer hard drives, and/or a portable RAM device.

In another embodiment, a portable media device having a processor, a storage element, a data interface, a speaker and a display element, wherein a user of the portable media device accesses a fitness program tailored to a profile of the user, wherein the fitness program includes a data acquisition module that receives fitness program selection information from the user, fitness program parameters input by the user, and data pertaining to physiological characteristics of the user that at least include height, weight, body fat percentage, and resting heart rate, wherein at least the data pertaining to physiological characteristics of the user are used to generate a user profile. The portable media device also includes fitness program operating module that retrieves a fitness program from the storage element based on the received fitness program selection information, wherein the fitness program operating module provides the selected fitness program to the user operable within the fitness program parameters input by the user and at least a portion of the user profile. The portable media device also includes an output module communicatively coupled to the fitness program operating module, wherein the output module transfers audio information to a speaker and video information to the display element, wherein the audio information corresponds to the video information as controlled by the selected fitness program.

In another embodiment, a method of providing a physical fitness routine configured as digital media operable with a mobile device, wherein the mobile device includes a processor configured for processing a plurality of programs operable via an operating system includes steps of initializing a fitness program operating module based on a user selection of the fitness program operating module, retrieving one or more user physiological parameters from a user interface configured with a mobile device, and retrieving one or more fitness parameters from the user interface. The method also includes steps of generating a user profile based on at least one of the one or more user physiological parameters and the one or more fitness parameters, retrieving a fitness instruction module from a storage element according to the user profile, and providing to a user of the mobile device audio fitness instruction, video fitness instruction, or a combination thereof, associated with the fitness instruction model.

Retrieving the one or more user physiological parameters from the user interface may include updating the physiological parameters through the user interface during the audio and video fitness instruction. Retrieving the one or more physiological parameters from the user interface may further include digitizing analog information input to the mobile device from the user. The analog information may include a heart rate, a blood pressure, a body temperature, a rate of oxygen consumption, a caloric expenditure, a pulmonary minute ventilation, caloric expenditure, or a combination thereof. Alternatively or at additionally, retrieving the one or more user physiological parameters from the user interface includes acquiring the physiological parameters from a touch screen interface, a keypad, a data interface, or accommodation thereof. Retrieving the one or more fitness parameters from the user interface may include acquiring the fitness parameters from a touch screen interface, a keypad, a data interface, or a combination thereof. The method may further include computing a recommended fitness instruction module based on the user profile, wherein computing the recommended fitness instruction includes consideration of the one or more users physiological parameters.

Providing the audio and video fitness instruction may include providing one or more music selections in addition to the audio fitness instruction. Providing the one or more music selections may include retrieving the one or more music selections from a digital media database. The digital media database may be configured with the storage element.

The mobile device is a cell phone, personal digital assistant, digital media player, a mobile gaming device, a laptop computer, or a tablet computer. The method may further include recording the fitness instruction on a processor readable media such as a DVD, a compact disc, a computer hard drives, and/or portable RAM devices.

In one embodiment, a mobile device provides one or more software programs to a user, wherein the mobile device includes a processor, a storage element, a data interface, an audio output, and a display element, wherein the mobile device provides one or more software programs to a user via an operating system. The at least one of the software programs is an instructional program that includes a user profile module that receives information about a user via the data interface, the display element, or both, wherein the user profile module configures a user profile based on the received information and wherein the user profile is stored with the storage element and includes at least one parameter entered by the user and an instruction module that processes the at least one instruction parameter and provides instruction to the user via the audio output and the display element based on the at least one instruction parameter of the user profile.

DETAILED DESCRIPTION OF THE DRAWINGS

Figures 1A, 1B:
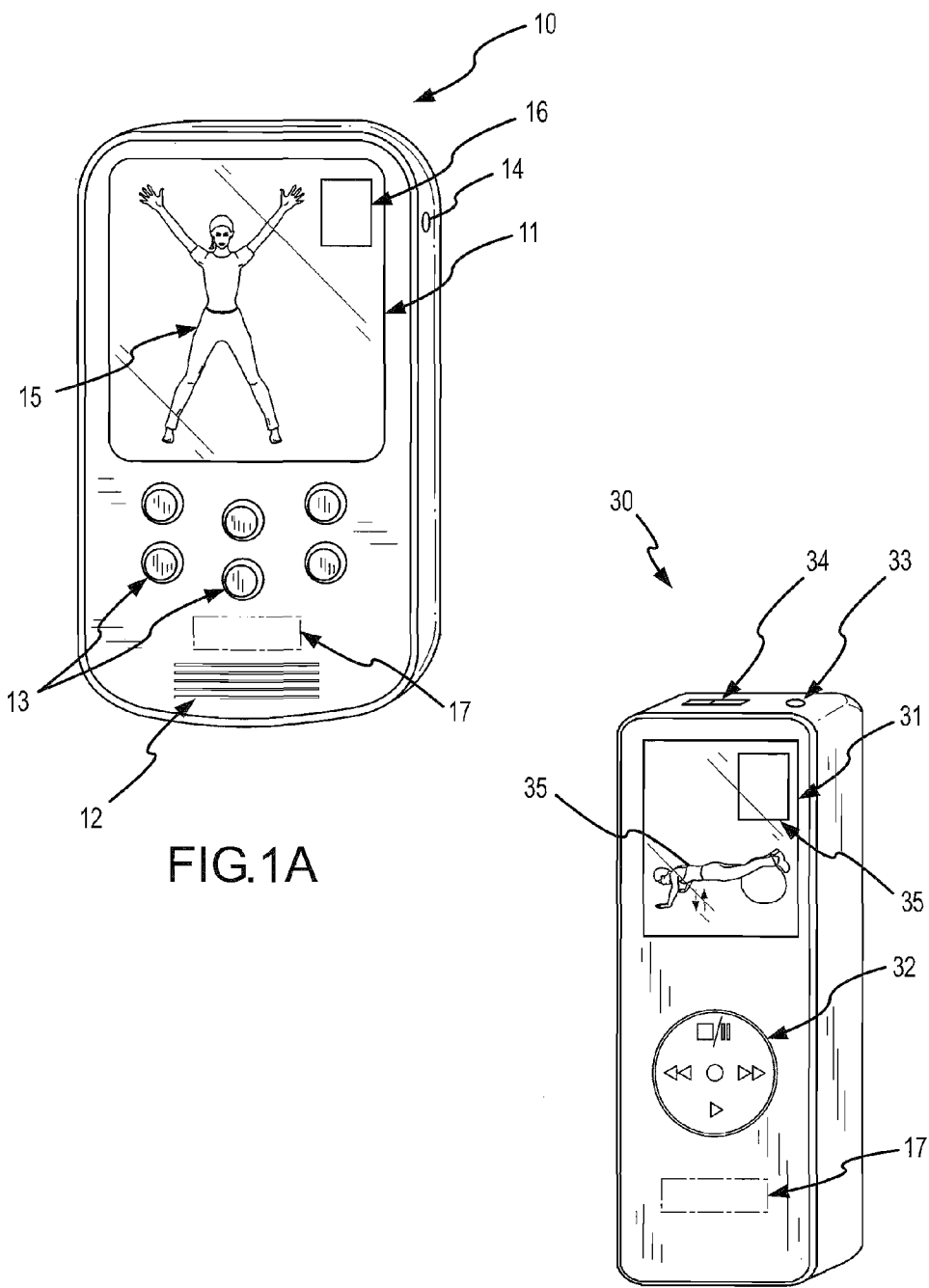
FIGS. 1A through 1D show mobile devices which may be used to support a physical fitness program.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope and spirit of the invention as defined by the claims.

Turning now to FIGS. 1A through 1D, these figures show exemplary mobile devices which may be used to support physical fitness program 17 (illustrated in phantom). In FIG. 1A, the physical fitness program 17 is configured with PDA 10 having display element 11. Display element 11 is used to display various video clips that demonstrate a physical fitness routine 15. In the context of a PDA, display element 11 may be configured in a variety of manners (e.g., liquid crystal display—LCD, touch screens, thin-film transistors—TFT, etc.). Additionally, physical fitness program 17 may be configured to display information 16 with display element 11. For example, information 16 may include the time remaining with a particular physical fitness routine and music selection associated with the routine. Other types of information may include information pertaining to the user's physiological characteristics, such as heart rate, body temperature, blood pressure, et cetera. For example, heart rate, blood pressure and body temperature may be those of a particular user at rest and/or during exercise. Audio (e.g., music voice over instruction) may also be included.

Common to PDAs are buttons 13 that are used to control various functions of PDA 10. For example, buttons 13 may be configured as a keypad for inputting characters and/or numbers to programs configured with PDA 10. Additionally, buttons 13 may be configured as a keypad for controlling the playback of a video (e.g., stop, pause, fast rewind, fast forward, play, zoom, etc.). PDA 10 may also be configured with audio components, such as audio jack 14 and/or speaker 12. For example, a user will likely wish to view and hear physical fitness routine 15 while exercising. As such, the user may position PDA 10 in the viewer's line of sight. Speaker 12 allows for the user to hear the physical fitness routine 15 while watching the physical fitness routine on display element 11. Similarly, the user may couple speakers to audio jack 14 or another audio port to hear the audio content of physical fitness routine 15.

PDA 10, as is typical among PDAs, is configured with a processor, a storage device (e.g., a mini computer hard drive, flash memory, RAM, etc.), and software. Among the software is PDA 10's operating system that allows various programs to operate or "run" with the PDA. In this regard, PDA 10 may run fitness program 17 to configure and present fitness routine 15 to a user. Details of such fitness instruction configuration are described below.

FIG. 1B shows a similar device in portable media player 30. Portable media players have become increasingly popular with the advent of "downloadable" digital music. For example, portable media players range from MP3 flash memory players, Apple Inc.'s iPods with hard drives, and video game players, such as Nintendo's Game Boy. Each of these devices has a processor generally configurable to operate physical fitness program 17 such that a physical fitness routine (e.g., physical fitness routine 35) may be displayed via display element 31. Additionally, information 35 relevant to the physical fitness routine may be displayed with display element 31. For example, information 35 may be the same as or similar to information 16 of FIG. 1A.

As with PDA 10 of FIG. 1A, portable media player 30 may also have associated user interface components, such as buttons (e.g., on-off/lock-unlock button 34), audio jacks (audio jack 33), et cetera. In this embodiment, portable media player 30 has features similar to an iPod. For example, portable media player 30 is configured with user interface wheel 32 that allows a user of the media player to controllably operate the media player (e.g., stop, pause, fast rewind, fast forward, play, zoom, etc.).

Figure 1C:
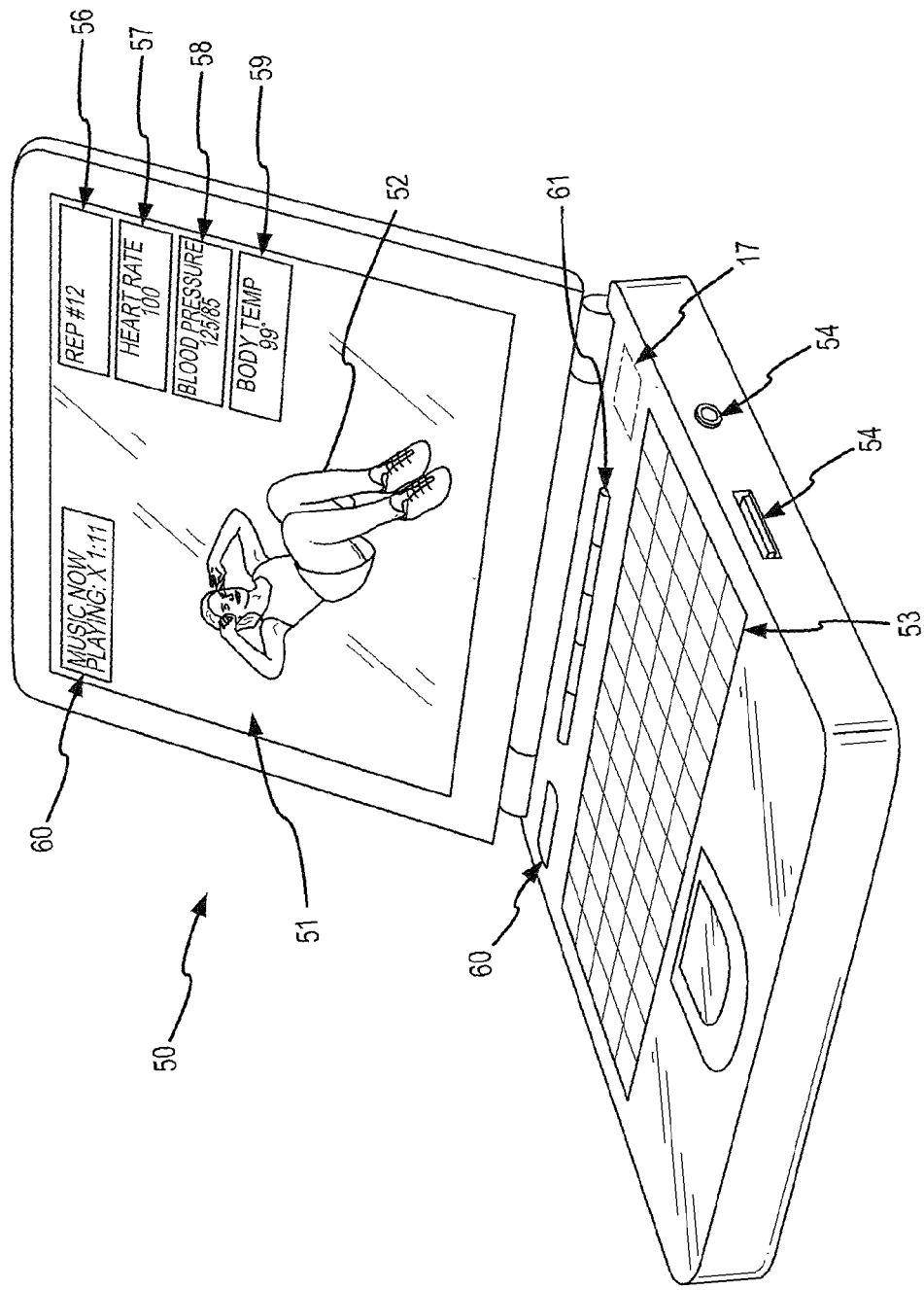

FIG. 1C illustrates an embodiment in which physical fitness program 17 is operable with laptop computer 50. Laptop computer 50 also displays a physical fitness routine 52 along with information, such as repetition number 56, heart rate 57, blood pressure 58, and body temperature 59. Generally, laptop computer 50 may have better processor performance than other types of mobile devices, such as PDAs and portable media players, because, among other reasons, of the larger physical size of the laptop (i.e., larger accommodations may allow for larger and thus more powerful processors). For these reasons, laptop computer 50 may be better suited for "real-time" updates of detected physiological parameters, such as heart rate 57, blood pressure 58, and body temperature 59. For example, sensors may be configured with the user of laptop computer 50 that detect physiological parameters of the user and feed analog signals regarding those parameters into laptop computer 50 via, e.g., communication port 54. In this regard, the software used to implement physical fitness routine 52 may be compatible heart rate devices, such as those produced by Polar Electro, Inc., so that the user can download and/or associate heart rate information from the heart rate device. In this regard, laptop computer 50 may process those analog signals by first converting them to digital format for subsequent processing. Laptop computer 50 may then display such information with display element 51 for use by the user of laptop computer 50. Examples of communication ports which may be suitable for communication port 54 include FireWire, Universal Serial Bus (USB), plug-and-play cards (e.g., PCMCIA), various RF interfaces (e.g., Bluetooth, WLAN, etc.), et cetera.

Additionally, laptop computer 50 may display a music selection 60 that is played with physical fitness routine 52. For example, a user may configure physical fitness routine 52 by entering various user parameters, such as desired physical fitness routine, number of repetitions, desired music to be associated with the physical fitness routine, et cetera. The physical fitness program 17 may configure the physical fitness routine 52 and provide background music during the course of instruction for physical fitness routine 52. The music selection may be displayed upon display element 51 to show the song that is playing (and/or the time remaining for the song) with the physical fitness routine.

Laptop computer 50, as is common to most laptop computers, has a plurality of user interface components. For example, laptop computer 50 is configured with keyboard 53. In this regard, a user of laptop 50 may enter various physical fitness parameters and/or physiological parameters to configure a user profile. Physical fitness program 17 may then process that user profile to configure/retrieve physical fitness routine 52 for the user. Additionally, laptop computer 50 may be configured with audio output 55 such that speakers may be coupled thereto for the audio portion of physical fitness routine 52. Other common features with laptop computer 50 include power button 60 and functional buttons 61. Examples of functional buttons 61 include volume control, music selection control, playback control, zoom, et cetera.

Figure 1D:
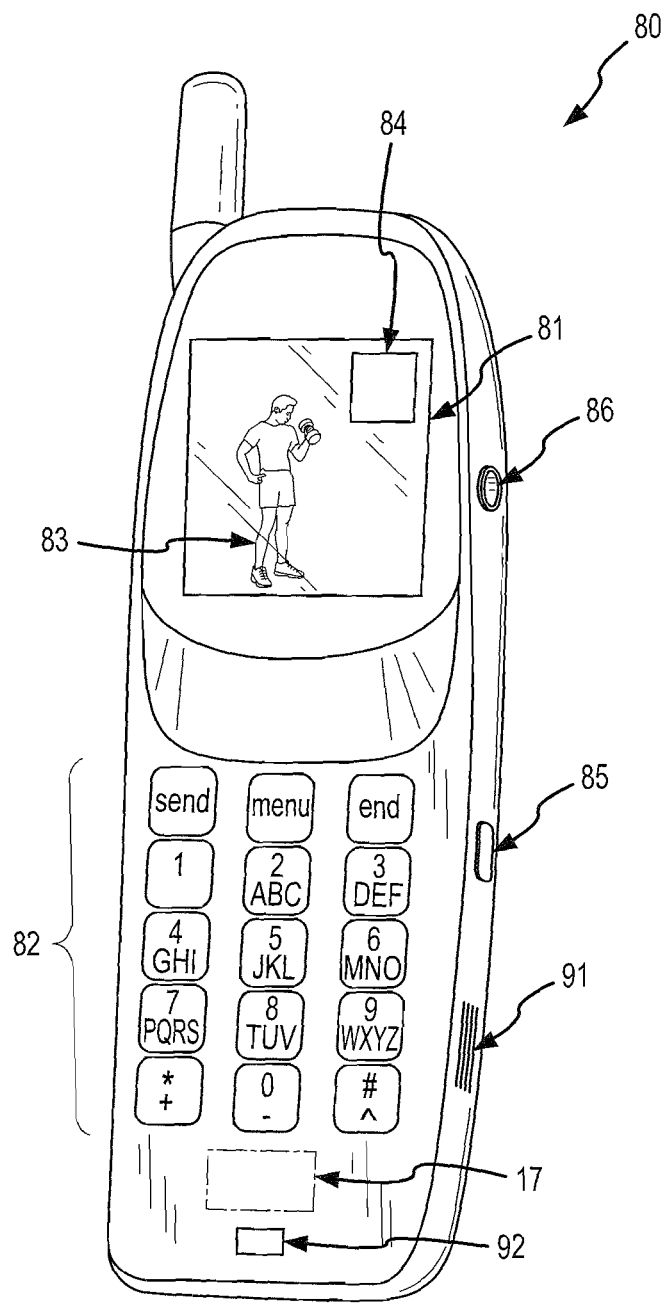

FIG. 1D shows an embodiment in which physical fitness program 17 is operable with mobile handset 80 (e.g., cell phone). As is common to most cell phones, mobile handset 80 is configured with keypad interface 82 for user. In this regard, the user may be able to enter physical fitness parameters and/or physiological parameters as described hereinabove to configure physical fitness routine 83 for display via interface 87. Additionally, physical fitness program 17 may process such information and display it to the user via display element 81 as information 84.

Mobile handset 80 may also be configured with various other controls (e.g., button 85) to control features such as volume for mobile handset 80. Additionally, mobile handset 80 may be configured with audio output 86 such that a user of mobile handset 80 may observe audio content associated with physical fitness routine 83. Alternatively, the user of mobile handset 80 may observe such audio content via other means. For example, many mobile handsets today are configured with Bluetooth technology which allows a user to wirelessly hear audio content associated with a phone call. This technology may also be used to observe other types of audio content, such as music, as many mobile handsets today are configured with digital music software (see e.g., Motorola RAZR and SLVR cell phones with iTunes by Apple Inc. configured therewith). Mobile handset 80 may also be configured with speaker 91 and microphone 92 for reasons that are generally obvious to cell phone users.

Depending on the processing capabilities of a particular mobile device, physiological characteristics may be updated in substantially real-time, as mentioned above. For example, a user may be equipped with sensors that monitor the user's ventilatory rate, heart rate, blood pressure, et cetera. The sensors may be communicatively coupled to the mobile device and processed by the mobile device for display via the associated display element (e.g., display elements 11, 31, 51, and 81). Alternatively or additionally, the mobile device may process this information to reconfigure an associated physical fitness program 17. For example, if the user is concerned about blood pressure, the user may initially configure the physical fitness program 17 with a not to exceed blood pressure value. A sensor configured with the user to monitor blood pressure may transfer information pertaining to the user's blood pressure during operation of the physical fitness program 17. When the user breaches the not to exceed blood pressure value, the physical fitness program 17 may reconfigure the operational physical fitness routine (e.g., physical fitness routines 15, 35, 51, and 83) such that the fitness routine either shuts down or scales back to lower the users blood pressure.

Those skilled in the art of medical sensor technology are readily familiar with configuring sensors that detect physiological parameters. Generally, the detected parameters are in analog form and are subsequently converted to a digital format for processing via a processor. This analog-to-digital conversion may take place in either the sensor or the mobile device. For example, when processing would be preferably offloaded from the mobile device, a sensor may be configured with an analog-to-digital converter that converts the detected analog signal into a digital format. The converted digital signal may then be transferred to the mobile device for processing described hereinabove. Alternatively, when processing associated with analog-to-digital conversion is not as taxing on a processor of the mobile device (e.g., in laptop computers with faster and more powerful processors), such conversion may be performed with the mobile device.

The embodiments hereinabove describe and illustrate manners in which physical fitness program 17 may operate with a device having a processor. The physical fitness routines illustrated in the above embodiments are varied to show different types of physical fitness instruction. For example, physical fitness routine 15 illustrates a person doing jumping jacks whereas physical fitness routine 35 illustrates a person doing push-ups with an exercise ball, in FIGS. 1A and B, respectively. FIGS. 1C and D respectively illustrate physical fitness routine 52 with a person doing sit-ups and physical fitness routine 83 with a person performing a bicep curl.

Accordingly, physical fitness program 17 is not intended to be limited to a particular type of physical fitness routine. Examples of other physical fitness routines include weight/strength training, aerobics, and various yoga routines/poses. Rather, physical fitness program 17 may be operable to select various software modules/components that may be loaded and controlled by physical fitness program 17 to display a particular physical fitness routine. For example, physical fitness program 17 may, based on user-entered parameters, configure a physical fitness routine for the user. Alternatively or additionally, the user selects exercises of his/her choice. Such is shown are described below in FIGS. 2 and 3.

Those skilled in the art, however, should readily recognize that the invention is not intended to be limited simply to physical fitness routines. Rather, other types of instruction may be incorporated into a program such as physical fitness program 17. For example, a person desirous of landscape instruction may wish to have that instruction delivered while in the act of landscaping. Accordingly, a program operating module operable with a mobile device may configure/retrieve landscape instruction for display via a display element and audio output as described hereinabove. In this regard, virtually any type of instruction may be incorporated into such a program. Other examples may include cooking, interior decorating, painting, language lessons (e.g., Spanish, French, German, etc.), et cetera.

Figure 2:
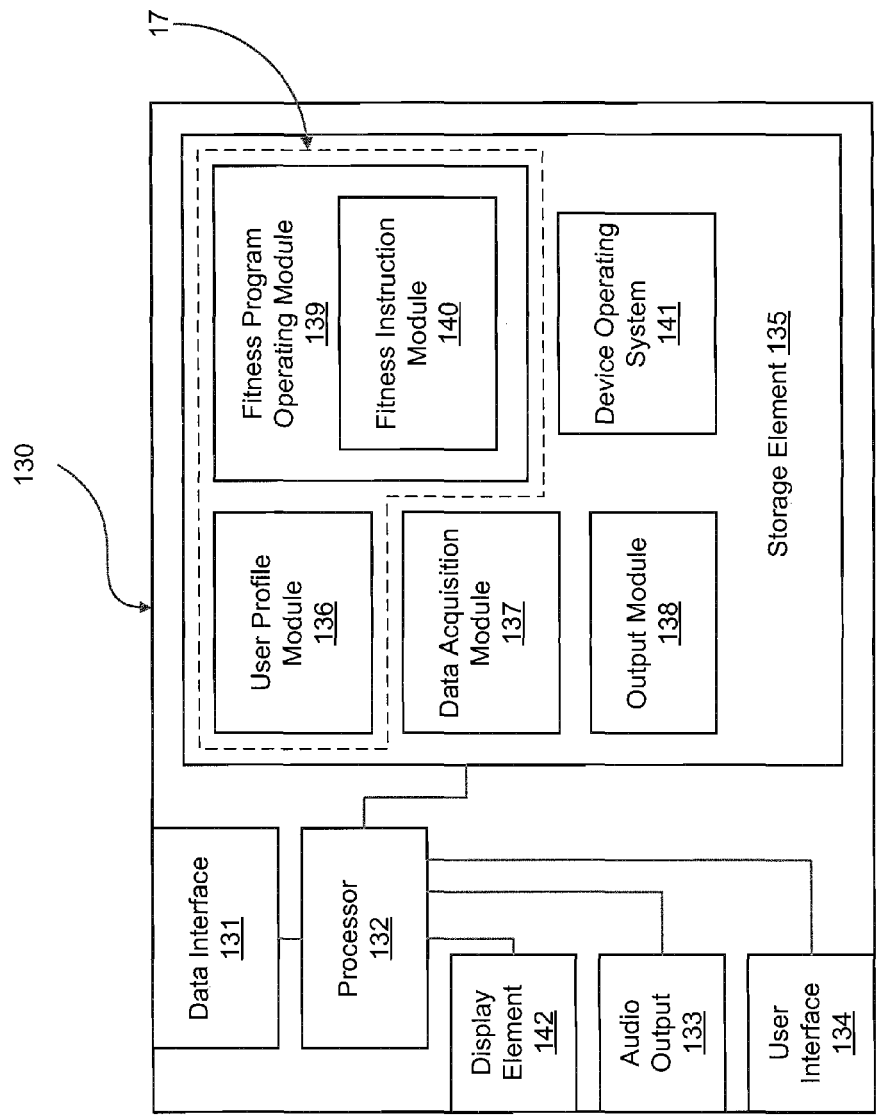
FIG. 2 is a block diagram of a mobile device configured with components and software that provide a physical fitness program.

FIG. 2 is a block diagram of general mobile device 130 configured with components and software that provide a physical fitness program. For example, mobile device 130 may be configured with processor 132 to process software instructions stored with storage element 135. In this regard, processor 132 maybe communicatively coupled to storage element 135 to receive and process software instructions stored therewith. The software instructions may include a device operating system 141 that provides individual software programs to operate with mobile device 130. Operating systems for computing devices such as mobile device 130 are well known to those skilled in the art.

Mobile device 130 may also be configured with audio output 133, display element 142, data interface 131, and user interface 134, each of which being communicatively coupled to processor 132. For example, user interface 134 and data interface 131 may each be configured for receiving information from a user which may be processed in conjunction with processor 132 processing user profile module 136. That is, processor 132 may be directed by software instructions of user profile module 136 to process received data from data interface 131 and/or user interface 134 to configure a user profile (described below in FIG. 3). In this regard, storage element 135 may also include software instructions in the form of data acquisition module 137. For example, data acquisition module 137 may be a firmware component (e.g., embedded software) common to mobile device, such as mobile device 130. Data acquisition module 137 may be configured for receiving electronic signals corresponding to data input through data interface 131 and/or user interface 134. Examples of user interface 134 may include keypads and buttons. Examples of data interface 131 may include virtually any type of communication interface that allows for data transfer, such as Ethernet, FireWire, USB, et cetera. Additionally, display element 142 may be configured to input information such that data acquisition module 137 may acquire data for use by user profile module 136. For example, display on a 142 may be a touch screen device in which a user may enter information by physically touching an LCD screen. Examples of such touch screen devices are generally common to PDAs. Those skilled in the art are readily familiar with such data acquisition components and software.

In regards to physical fitness program 17 described in FIGS. 1A-D, the physical fitness program may be embodied by at least user profile module 136 and fitness program operating module 139. As mentioned, user profile module 136 may receive information from data acquisition module 137. User profile module 136 may then generate a user profile for use by fitness program operating module 139. For example, user profile module 136 may receive parameters from a user that may be used to customize or configure a particular physical fitness routine for the user. In other words, the user may enter parameters such as intensity (e.g., load, number of sets, number of repetitions per set, percentage of maximal heart rate, etc.), duration, etc. and/or the type of exercise wherein such terms may be relevant so as to configure a particular physical fitness routine for the user. In this regard, fitness program operating module 139 may process the user profile from user profile module 136 to load fitness instruction module 140 that corresponds to the type of exercise entered by the user. The parameters (e.g., number of repetitions, duration, etc.) may then be processed with fitness instruction module 140 to deliver a customized physical fitness routine to the user.

Alternatively or additionally, the user profile may be processed to simply retrieve fitness instruction module 140. For example, fitness instruction module 140 may be a preconfigured module or even a fitness program designed by user which, upon processing of the user profile, loads into fitness program operating module 139. Fitness program operating module 139 thereby runs fitness instruction module 140 to deliver a preconfigured fitness instruction that may be less personalized that described hereinabove. The invention, however, is not intended to be limited to any particular type of configurable or preconfigured instruction. Additional details of such personalized fitness routine configurations and preconfigured fitness instruction modules are described below in FIG. 3.

Delivery of the physical fitness routine may consist of transferring audio and/or video information to output module 138. For example, output module 138 may be a software program configured with mobile device 130. Video clip data and associated audio data may be transferred to output module 138 such that, when processed by processor 132, video is displayed with display element 142 and audio is output through audio output 133.

Data acquisition module 137 may be configured to retrieve other parameters. For example, certain physiological parameters of the user may be input to mobile device 130 via data interface 131. These parameters may be real-time physiological parameters of the user acquired from sensors that the user wears during the physical fitness routine. The sensors may be configured to monitor physiological parameters such as blood pressure, heart rate, body temperature, et cetera. As such, and acquisition module 137 may process real-time physiological parameters of the user such that the user profile can be updated by user profile module 136 for subsequent control of fitness instruction module 140. That is, user profile module 136 may transfer the user profile to fitness program operating module 139 such that the fitness instruction module is adjusted (e.g., scaled up, scaled down, or ceased) based on breaches of certain parameter thresholds.

To illustrate, when the user's heart rate increases past a predetermined heart rate threshold during a particular fitness instruction presented by fitness instruction model 140, fitness program operating module 139 may scale down or stop fitness instruction module 140 so that the user's health or desired exercise intensity is not jeopardized. Alternatively, when the user's heart rate is below a particular threshold, fitness program operating module 139 may scale up, for example, the repetition rate of the presented fitness instruction so that the user takes full advantage of the cardiopulmonary effects. Such scaling of may be either automatic or in response to an automatically generated request by the fitness program operating module 139 to the user. For example, fitness program operating module 139 may generate a request which is transferred to output module 138 for display via display element 142. In this regard, the user may choose to scale up the presented fitness instruction.

The invention is not intended to be limited to sensed physiological parameters that are updated in real time. Rather, other embodiments may have a user inputting physiological parameters through user interface 134 and/or display element 142. For example, the user may wish to configure a physical fitness routine based on a priori knowledge of the user's heart rate and blood pressure. Such knowledge may be based on the user's heart at rest (i.e., during little physical exertion), which is generally a measurement of fitness. The user may input this information with user profile module 136 via user interface 134. That is, processor 132 may process data acquisition module 137 to acquire user-entered information from user interface 134. Processor 132 may thereby process user profile module 136 with this information to generate the user profile and subsequently configure a physical fitness routine (e.g., via fitness program operating module 139 and fitness instruction module 140).

Figure 3:
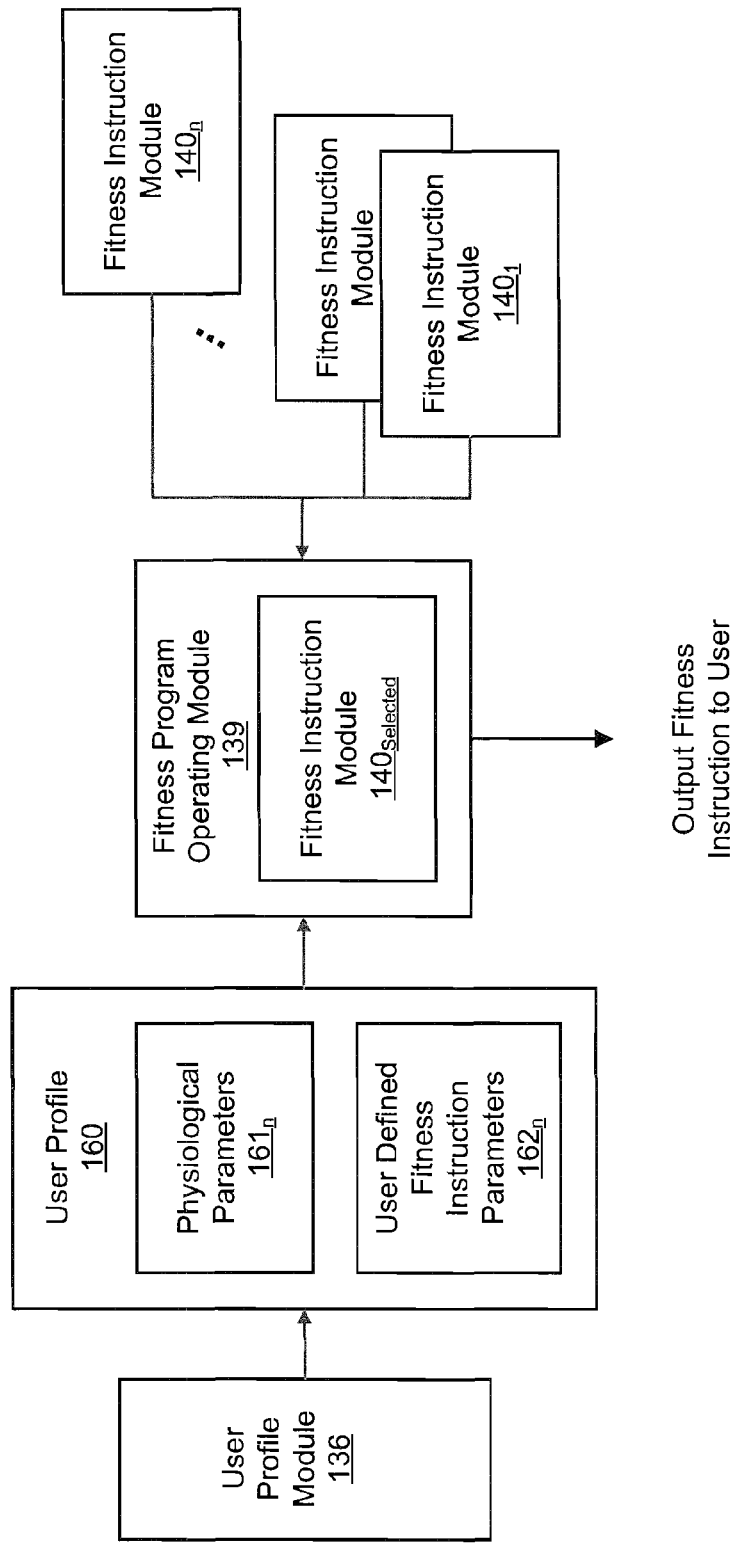
FIG. 3 is a block diagram of various software modules and their associations within the physical fitness program module.

FIG. 3 is a block diagram of various software modules and their associations within physical fitness program operating module 139. As stated hereinabove, user profile module 136 receives information from a data acquisition module. This data may be in the form of physiological parameters 161 of the user and/or specified physical fitness routine parameters (i.e., user-defined fitness instruction parameters 162). User profile module 136 then configures 160 for use by fitness program operating module 139.

Fitness program operating under 139 may retrieve from storage element 135 a particular fitness instruction module 140. For example, storage element 135 may be configured to store a plurality of fitness instruction modules$_{1 \ldots n}$ each of which being configured to provide a particular type of fitness instruction (e.g., cardiopulmonary exercise, weight lifting, etc. or various combinations thereof). Based on user-defined fitness instruction parameters 162 as entered by the user, fitness program operating module 139 selects a fitness instruction module 140 (illustrated as fitness instruction module 140$_{selected}$) that the fitness program operating module determines is most appropriate for the user. For example, if the user selects a cardiopulmonary fitness routine, fitness program operating module 139 may retrieve from storage element 135 the cardiopulmonary fitness routine that corresponds to the parameters entered by the user.

Additionally, fitness program operating module 139 may retrieve various parameters from the user profile that are associated with the selected fitness instruction module 140. For example, the user may select a fitness instruction module that is adjustable in duration. Accordingly, the user may enter the duration for the particular fitness instruction which is subsequently processed with user profile 160. Fitness program operating module 139 may process this entered duration value to provide control parameters for fitness instruction module 140$_{selected}$.

As stated hereinabove, the invention is not intended to be limited to mere retrieval of fitness instruction modules. For example, fitness program operating module 139 may configure a fitness instruction module 140 based on aspects of various fitness instruction as well as the user profile. That is, fitness program operating module 139 may arrange video and audio clips of fitness instruction according to user-defined instruction parameters 162 and/or physiological parameters 161 that customize a physical fitness routine for the user based on those parameters. Alternatively or additionally, the fitness routines can be self-selecting with video clips of exercises. Moreover, the physical fitness routine may be output to a computer readable media, such as a DVD or CD.

Figure 4:
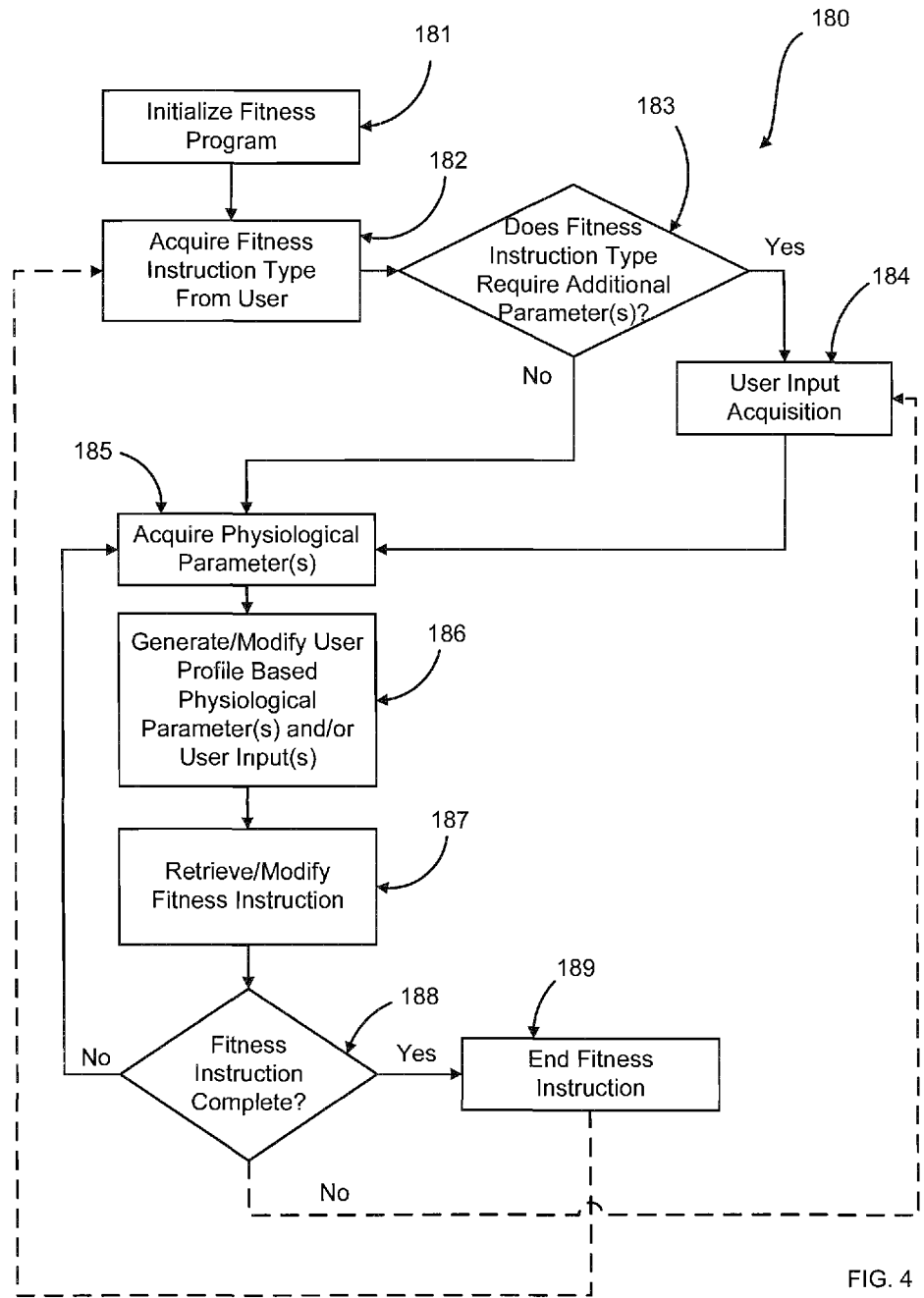
FIG. 4 is a flow chart illustrating a process associated with a physical fitness software program.

FIG. 4 is a flow chart illustrating process 180 associated with a physical fitness software program, such as physical fitness program 17 described hereinabove. Process 180 begins when the physical fitness program is initialized, in process element 181. For example, since the physical fitness program generally requires display of video content in the fitness instruction, a physical fitness program is configured with a computing device having a display element, such as a touch screen interface or LCD. The display element may, as is generally known, be used to navigate to the physical fitness program (i.e., via the operating system interface) to start the physical fitness program.

Once the fitness program is initialized, the fitness program may generate a request to the user to acquire a desired fitness instruction type from the user, in process element 182. The program may prompt the user to select from a plurality of fitness instruction modules, such as fitness instruction modules 140 of FIG. 3. Based on the user's entry, a fitness program may select and/or configure the fitness instruction for delivery to the user. In this regard, the fitness program may determine whether the fitness instruction type requires additional parameters, in process element 183. For example, a fitness instruction such as "running in place" may request, from the user, a duration parameter for the fitness instruction. Accordingly, the user may be allowed to limit the running in place fitness instruction to an amount of available time for the user and/or so as to not exceed the user's abilities.

If the fitness instruction type requires additional parameters, the fitness program may acquire user input, in process element 184, based on a generated request. Subsequently, a fitness program may acquire physiological parameters of the user, in process element 185. Similarly, if the fitness instruction does not require additional parameters, process 180 may traverse to process element 185 to acquire physiological parameters of the user.

As stated herein above, physiological parameters may include, for example, heart rate, blood pressure, body temperature, et cetera. These parameters may be acquired through a user interface of a device in which the fitness program is configured. That is, the fitness program may be configured with a mobile device, such as a PDA or a laptop computer that allows the user to enter parameters to the fitness program. In this regard, the fitness program may request such information from the user to assist in a configuration of a particular fitness instruction for the user. For example, the fitness program may generate a user profile based on physiological parameters and/or other user inputs (e.g., fitness instruction parameters), in process element 186. The fitness program may then retrieve and/or modify a fitness instruction in process element 187 as described herein above.

Routinely throughout the fitness instruction, the fitness program may ascertain whether the fitness instruction is complete, in process element 188. For example, the fitness program may periodically interrogate the fitness instruction based on the user entered parameters to ensure that the fitness instruction does not operate beyond those parameters. To illustrate, the fitness program may determine when a duration value particular fitness instruction has been exceeded to end or shut down the fitness instruction, in process element 189. Additionally, when a fitness program determines that the parameters of the fitness program have not been exceeded, the fitness program may acquire additional physiological parameters. For example, the user of the fitness program may be equipped with sensors that detect various physiological parameters of the user. These physiological parameters may be transferred to the mobile device for processing by the fitness program so that the user profile may be modified, in process element 186, and subsequently modify the operable fitness instruction, in process element 187.

Additionally or alternatively, if the fitness instruction is not complete, process 180 may allow a user to traverse to process element 184 to input other fitness instruction parameters. For example, during a particular physical fitness instruction, the user may wish to modify the fitness instruction. Such modifications may include changing duration values, repetition values, music selections, et cetera. The fitness program would acquire these entered modifications and update the user profile such that the fitness instruction may be modified in process element 187.

When the fitness program ends an operable fitness instruction in process element 189, the fitness program may similarly end (i.e., shut down) or acquire an additional fitness instruction type from the user. For example, when the fitness instruction has completed, the user may choose to continue physical fitness training by selecting another physical fitness instruction. Accordingly, the fitness program may acquire another fitness instruction type from the user, in process element 182, to continue process 180.

Although one embodiment has been shown and described in process 180, those skilled in the art should readily recognize that the invention is not intended to be limited to the illustrated embodiment. Rather, process 180 may be configured in other ways, such as the rearranging of process elements, that fall within the scope and spirit of the invention. For example, a fitness program may wish to acquire physiological parameters (process element 185) prior to user input acquisition (process element 184). These changes in parameter acquisition, as well as other modifications to process 180, are intended to be included within the scope of the invention.

The various software modules described herein may be configured as embedded software modules and/or higher level software modules. Such software, processors, storage elements, display units, and video data such as JPEG and MPEG are known to those skilled in the art. The various systems and methods described herein may provide certain advantages to the user. For example, the user may train according to a physical fitness training regimen that is provided by a professional physical fitness trainer, without the burden of visiting the physical fitness professional. In this regard, the software module may be updatable such that training regimens may be updated (e.g., as the user progresses into advanced training regimens).

Figure 5:
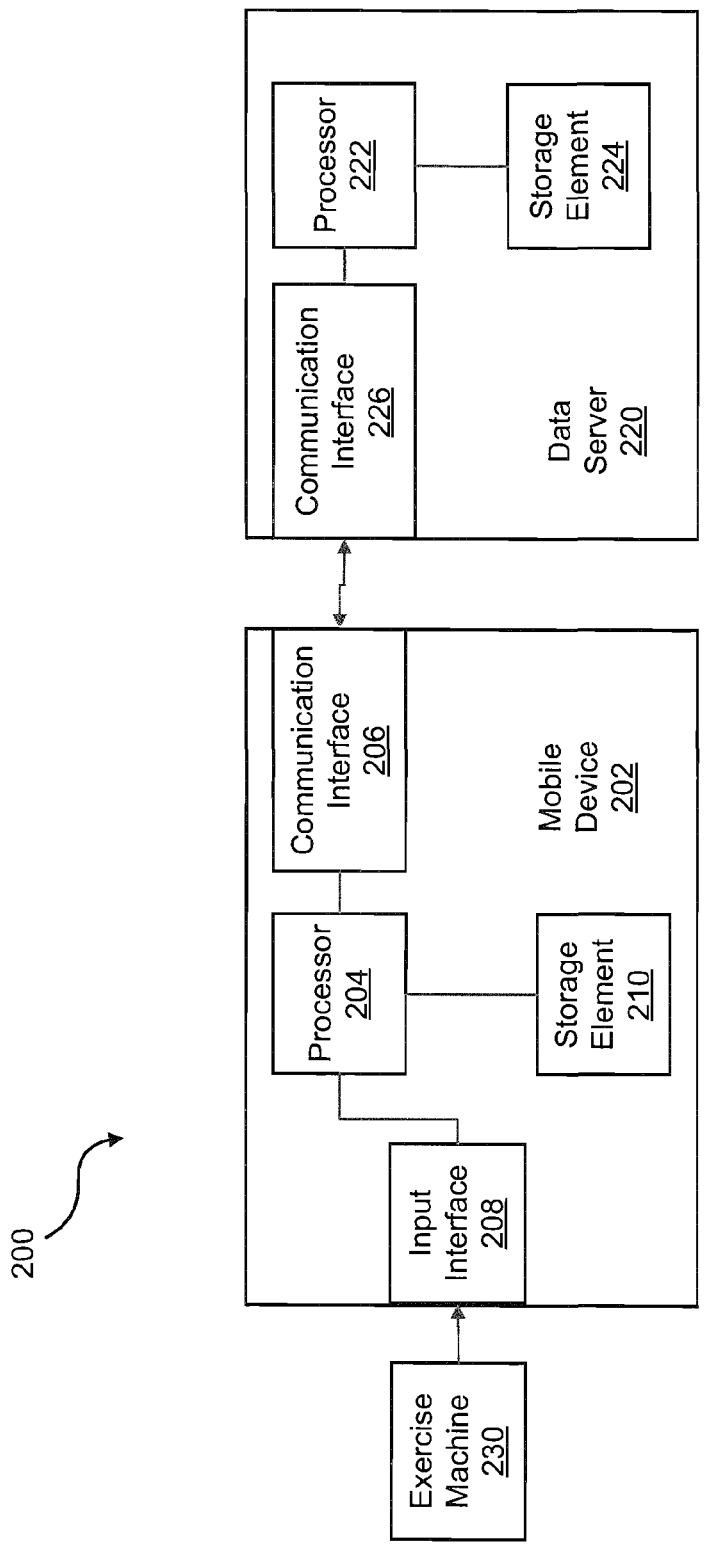
FIG. 5 is a block diagram illustrating a system for downloading instructional video files pertaining to the operation of an exercise machine to a mobile device from a data server.

FIG. 5 is a block diagram illustrating a system 200 for downloading instructional video files pertaining to the operation of an exercise machine 230 to a mobile device 202 from a data server 220. The system includes a mobile device 202, which contains components similar to those described hereinabove, and a data server 220. Mobile device 202 also includes an input interface 208, which is used to select an exercise machine 230 that the user would like to learn to use. For example, the input interface 208 may be a barcode scanner that can be used to scan a barcode placed on the exercise machine 230. Alternatively, the input interface 208 could be any device or function that is capable of identifying a particular exercise machine 230. As an example, a keypad on the mobile device 202 may be used to identify the exercise machine 230 by name or an identification number. In another example, a camera may be attached to or embedded in the mobile device 202, where a photo is used to identify the exercise machine 230. Mobile device 202 also contains processor 204 and operating system (not shown) for controlling the operation of the system. Processor 204 is communicatively attached to communication interface 206, which is used to send and receive data between the mobile device 202 and a data server 220. Communication interface 206 may be any suitable data transfer interface including USB, WiFi, Bluetooth, Cellular, et cetera.

Mobile device 202 sends a request for a video file to data server 220 which informs the data server 220 of which video file to send (e.g., by including the barcode number of the exercise machine). This request may also contain various other parameters (e.g., file type, file size, audio preferences, et cetera). The data server 220 is communicatively attached to a communication interface 226, which is configured to communicate with mobile device 202. After communication interface 226 receives the request from the mobile device 202, processor 222 in the data server 220 interprets the request from mobile device 202 and retrieves the corresponding video file from storage element 224. The requested video file is transferred from data server 220 to mobile device 202 via communication interface 206, 226. Mobile device 202 then stores the video file in storage element 210 for viewing on the display element of the mobile device 202, as similarly described hereinabove.

Note that users are not limited to selecting a single exercise machine when requesting a video. A user may select any or all of the exercise machines at a particular health club. Additionally, although not necessary, the data server will usually be operated by the particular health club that houses the exercise machines. Moreover, the invention is not intended to be limited to the retrieval of instructional videos for the operation of exercise machines. For example, other instructional videos that may be downloaded using this system include strength exercises, yoga poses, rehabilitation exercises, et cetera.

Additionally, the instructional videos may be output to a computer readable media that enables the user to observe the videos at a later time. For example, software may be configured to perform that described above and allow for a personalized physical fitness routine to be stored on a DVD such that the personalized physical fitness routine may be viewed later on a television or a computer. In this regard, the software may be configured to operate on mobile device 202 and/or server 220.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A fitness system, comprising:

a mobile device comprising a graphical user interface, wherein the mobile device is operable to connect to a data network, to download a fitness video from a communication network, and to display the video via the via the graphical user interface, the mobile device further comprising a software module and a processor, wherein the software module comprises instructions that direct the processor of the mobile device to present a display to a user via the graphical user interface, to retrieve physiological parameters of the user through the presented display, to retrieve a fitness routine preferred by the user, and to configure the fitness routine based on the retrieved physiological parameters and the fitness video; and a server communicatively coupled to the mobile device through the communication network and operable to store the fitness video, to transfer the fitness video to the mobile device, to maintain a user profile of the user that includes the retrieved physiological parameters, to monitor live physiological parameters of the user during the fitness routine by the user through the mobile device, and to direct the mobile device to alter the fitness routine based on the monitored physiological parameters, wherein the retrieved physiological parameters comprise the user's age, sex, weight, height, and body fat percentage, wherein the monitored physiological parameters of the user comprise resting heart of the user, active heart rate of the user during the fitness routine, blood pressure of the user, and body temperature of the user, wherein the server is further operable to update the user profile based on the monitored physiological parameters of the user, and to recommend another fitness routine based on the user profile.

* * * * *